United States Patent
Aslan et al.

(10) Patent No.: US 12,156,932 B2
(45) Date of Patent: Dec. 3, 2024

(54) HAIR COSMETIC COMPOSITIONS CONTAINING CATIONIC COMPOUNDS, PANTHENOL, AND OILS

(71) Applicant: L'OREAL, Paris (FR)

(72) Inventors: Seyma Aslan, Clifton, NJ (US); Rita Chokshi, Monroe Township, NJ (US); Anand Ramchandra MAhadeshwar, Mumbai (IN); Marie Huynh, Monmouth Junction, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/588,194

(22) Filed: Sep. 30, 2019

(65) Prior Publication Data
US 2021/0093545 A1    Apr. 1, 2021

(51) Int. Cl.
| | |
|---|---|
| *A61K 8/34* | (2006.01) |
| *A61K 8/41* | (2006.01) |
| *A61K 8/42* | (2006.01) |
| *A61K 8/81* | (2006.01) |
| *A61K 8/898* | (2006.01) |
| *A61K 8/92* | (2006.01) |
| *A61Q 5/00* | (2006.01) |

(52) U.S. Cl.
CPC ............ *A61K 8/8176* (2013.01); *A61K 8/342* (2013.01); *A61K 8/416* (2013.01); *A61K 8/42* (2013.01); *A61K 8/898* (2013.01); *A61K 8/922* (2013.01); *A61Q 5/00* (2013.01)

(58) Field of Classification Search
None
See application file for complete search history.

(56) References Cited

U.S. PATENT DOCUMENTS

| | | | | |
|---|---|---|---|---|
| 9,125,838 | B2 * | 9/2015 | Hunter | A61K 8/73 |
| 2007/0081965 | A1 * | 4/2007 | Daou | A61K 8/19 |
| | | | | 424/70.28 |
| 2008/0085254 | A1 * | 4/2008 | Nguyen | A61K 8/922 |
| | | | | 424/70.23 |
| 2012/0103357 | A1 * | 5/2012 | Hoffmann | A61K 8/26 |
| | | | | 132/202 |
| 2014/0246041 | A1 * | 9/2014 | Krueger | A61K 8/466 |
| | | | | 424/70.28 |
| 2017/0281522 | A1 * | 10/2017 | Gevgilili | A61K 8/342 |
| 2017/0340547 | A1 * | 11/2017 | Foerster | B05B 9/002 |
| 2018/0055751 | A1 | 3/2018 | Gevgilili et al. | |

FOREIGN PATENT DOCUMENTS

DE    10 2013 212623 A1    3/2014

OTHER PUBLICATIONS

International Search Report and Written Opinion issued on Dec. 14, 2020 for corresponding PCT Application No. PCT/US2020/053019.

* cited by examiner

*Primary Examiner* — Nicole P Babson
*Assistant Examiner* — Lori K Mattison
(74) *Attorney, Agent, or Firm* — POLSINELLI PC

(57) ABSTRACT

The instant disclosure relates to hair cosmetic compositions that include a cationic vinylpyrrolidone copolymer, a cationic thickening agent comprising at least one unit derived from acrylic or methacrylic acid, a cationic surfactant, including a cationizable surfactant; a fatty alcohol, present in an amount of not more than about 3 wt. %; panthenol, an amino functionalized silicone, a plant or vegetable oil, present in an amount of not more than about 4.5 wt. %; and water. Methods for using such hair cosmetic compositions are also provided.

19 Claims, 1 Drawing Sheet

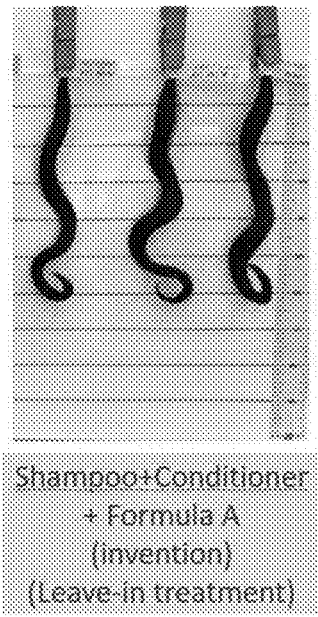

HAIR COSMETIC COMPOSITIONS CONTAINING CATIONIC COMPOUNDS, PANTHENOL, AND OILS

FIELD OF THE DISCLOSURE

The instant disclosure relates to hair cosmetic compositions that are particularly useful for improving the quality of hair, in particular, curly hair, and which can impart durable styling/shaping attributes to hair. Also disclosed are methods for using the hair cosmetic compositions.

BACKGROUND

Many consumers desire to use cosmetic and care compositions that enhance the appearance of keratinous substrates such as hair, e.g., by changing the color, style, and/or shape of the hair, and/or by imparting various cosmetic properties to hair, such as shine and conditioning. Many of the known compositions and processes for enhancing or preserving the appearance of hair involve chemical treatments to the hair.

The process of changing the color of hair, for example, can involve depositing an artificial color onto the hair which provides a different shade or color to the hair, and/or lifting the color of the hair, such as lightening the color of dark hair to lighter shades, which m requires the use of oxidizing agents.

Additionally, there are many techniques and compositions for styling or altering the shape of hair. For example, hair care products referred to as "hair relaxers" or "hair straighteners" can relax or straighten curly or kinky hair, including wavy hair. Straightening or relaxing the curls of very curly hair may increase the manageability and ease of styling of such hair. Compositions for permanent waving the hair will impart a curl or a wave to otherwise straight hair. Different types of compositions can be applied onto hair in order to change its shape and make it more manageable, such as alkaline and acidic compositions. Hair relaxers, straighteners, perms, and/or waves may either be applied in a hair salon by a professional or in the home by the individual consumer.

While dyeing or color lifting compositions can effectively alter the color of hair, and relaxing, straightening, perming, and waving compositions can effectively alter the shape of the hair, these chemical treatments can damage the hair fibers and/or irritate the scalp. Thus, in order to reduce or avoid damage to hair, as well as to improve the cosmetic performance of the compositions, different types of hair styling products have been developed by manufacturers that are aimed to help consumers achieve a desired look, including one or more of fuller hair, thicker hair, sleek and straight hair, frizz-free hair, and defined curls. These products are typically provided in forms that are applied after the shampooing and conditioning processes are completed.

Increasingly, consumers also seek hair products that have a natural look and feel, a light-weight feel, while imparting longer-lasting styling or shaping benefits to hair. Further, consumers seek products that offer multiple benefits, for example, combining frizz reduction and style hold with softening, elongation or lengthening effects while still providing good curl definition. Moreover, consumers desire hair products that can protect hair from external factors such as high humidity which causes the hair to become very frizzy, unmanageable, and lose its shape and style or such as mechanical or physical or other external stresses on hair.

One important property sought by consumers of such products is their ability to provide longer lasting style or shape to the hair; i.e., a style or shape that lasts overnight or can easily be regained when the consumer wakes up with no or minimal reapplication of the styling product and/or with no or minimal manipulation of the hair to restyle or re-shape the hair and/or with no utilization of mechanical or physical styling devices such as hair rollers, hair pins and clips, head bands, or head caps. Thus, many consumers seek hair products which have excellent style memory. While different technologies and products exist in the market for hair styling products, there is still a need for improvement in these areas as well as at the same time, the need to provide caring benefits that are not typically found in a styling product.

Thus, the object of this invention is related to a composition and method of treating hair utilizing hair compositions which will deliver both caring and styling/shaping benefits that are long lasting or durable and can be maintained overnight or when the hair is subjected to changes in the hair shape or style or configuration, and/or to disturbance of the hair fibers and/or to movement of the hair fibers as a result of sleeping or lying down and resting the head on a bed or other surface or the back part of a seat and/or as a result of wearing a head cap or cover. Such styling/shaping benefits are for example, curl definition, as frizz control, discipline, shape control/hold, softness, smoothness, shine, natural feel, hydration, and light weight feel.

The object of the invention is also to deliver all other styling benefits that curly haired consumers desire on a daily basis: curl definition, moisture, conditioning, hold, frizz control, curl/shape retention, curl pick up, moisture to curls, and not leaving the curls feeling greasy or stiff. The composition from such an invention can be applied on wet or damp hair using various techniques such as "wash and go" or "twist out" methods. "Wash and go" involves applying the product, section by section, to wet or damp hair and letting it air dry. The "twist out" method involves manipulating the curl pattern in order to provide elongation while maintaining other styling benefits. It can be done by applying the product on wet hair and twisting small sections of the hair and letting it air dry.

The invention is particularly useful for treating and providing the described properties to curly hair (of varying degrees of curl) and to wavy hair.

SUMMARY OF THE DISCLOSURE

It has surprisingly been found that compositions and methods of treating hair according to the present invention impart durable styling/shaping attributes, including curl definition, curl retention, curl pick up, frizz control, volume control, control/hold, discipline, as well as other cosmetic benefits such as fast/easy styling or shaping, hydration, moisture, and smoothness to the hair, while still providing a light weight feel and a clean feel (non-greasy, non-oily) to the hair. These attributes were achieved even after the hair treated with the composition of the invention was subjected to changes in the hair shape or style or configuration, and/or to disturbance of the hair fibers and/or to movement of the hair fibers as a result of sleeping or lying down and resting the head on a bed or other surface or the back part of a seat and/or as a result of wearing a head cap or cover for at least 30 minutes up to several hours or overnight.

One aspect of the invention pertains to a hair cosmetic composition comprising:
(a) at least one cationic vinylpyrrolidone copolymer;
(b) at least one cationic thickening agent comprising at least one unit derived from acrylic or methacrylic acid;

(c) at least one cationic surfactant, including a cationizable surfactant;
(d) at least one fatty alcohol, present in an amount of not more than about 3 wt. %;
(e) panthenol;
(f) at least one amino functionalized silicone;
(g) at least one plant or vegetable oil, present in an amount of not more than about 4.5 wt. %; and
(h) water;
all weights being based on the total weight of the hair cosmetic composition.

Another aspect of the invention pertains to methods of treating hair, such as styling or shaping hair, including imparting durable style or shape to hair. In some embodiments, the method comprises applying any of the compositions described herein to hair. In one or more embodiments, the composition is applied to hair, including curly hair, as part of a hair styling/shaping or caring routine. In some embodiments, the composition is applied after treating the hair with a shampoo and/or conditioner and/or a masque (mask).

BRIEF DESCRIPTION OF THE DRAWING

Implementation of the present technology will now be described, by way of example only, with reference to the attached FIGURE, wherein:

FIG. 1 includes pictures of hair swatches treated with test formulas: one set of swatches was treated with a comparative formula and another set of swatches was treated with the inventive formula.

It should be understood that the various aspects are not limited to the arrangements and instrumentality shown in the drawings.

DETAILED DESCRIPTION OF THE DISCLOSURE

The term "hair cosmetic composition" encompasses many types of compositions for application to the hair, for example, hair lotions, hair emulsion creams, hair gel creams, hair conditioners, hair masques (masks), etc., which can be used either as leave-on or rinse-off treatments or products. A hair cosmetic composition according to the invention is characterized by its ability to provide a cosmetic (such as styling/shaping and caring) benefit to the hair. Non-limiting examples of benefits that can be imparted by the compositions of the present invention to hair include long lasting or durable style/shape, as well as one or more of frizz control, curl definition, curl retention, curl pick-up, styling/shaping, discipline, volume control, hold/control, manageability, smoothness, softness, suppleness, hydration (does not feel dry) and natural feel. At the same time, even when the compositions of the present disclosure contain fatty compounds such as fatty alcohols, silicones, and plant- or vegetable-based oils, surprisingly, a light weight feel and a clean feel (non-greasy, non-oily) are imparted to the hair.

The hair cosmetic compositions of the instant disclosure typically include:
(a) at least one cationic vinylpyrrolidone copolymer;
(b) at least one cationic thickening agent comprising at least one unit derived from acrylic or methacrylic acid;
(c) at least one cationic surfactant, including a cationizable surfactant;
(d) at least one fatty alcohol, present in an amount of not more than about 3 wt. %;
(e) panthenol;
(f) at least one amino functionalized silicone;
(g) at least one plant or vegetable oil, present in an amount of not more than about 4.5 wt. %; and
(h) water;
all weights being based on the total weight of the hair cosmetic composition.

In an embodiment, the weight ratio of the total amount of the at least one cationic vinylpyrrolidone copolymer and the at least one cationic thickening agent comprising at least one unit derived from acrylic or methacrylic acid to the total amount of the at least one amino functionalized silicone and to the at least one plant or vegetable oils is about 0.2 to about 0.8.

In an embodiment, the at least one cationic vinylpyrrolidone copolymer is selected from copolymers of vinylpyrrolidone and at least one monomer selected from the group consisting of (meth)acrylic acid; (meth)acrylates; unsaturated hydrocarbons; and vinyl monomers.

In an embodiment, the at least one cationic vinylpyrrolidone copolymer is VP/Dimethylaminoethylmethacrylate Copolymer.

In an embodiment, the at least one cationic vinylpyrrolidone copolymer is present in an amount of greater than 0.4 to about 2 wt. %, preferably, about 0.6 to about 1.5 wt. %, more preferably, about 0.6 to about 1 wt. %, or even more preferably, about 0.6 to about 0.8 wt. %, based on the total weight of the hair cosmetic composition.

In an embodiment, the at least one cationic thickening agent comprising at least one unit derived from acrylic or methacrylic acid is selected from polymers resulting from the polymerization of one or more monomers having the structure (I):

$$CH_2=C(R'_3)-COO-A_1-N^+-R'_4R'_5R'_6X_1^- \quad (I)$$

in which:
R'$_3$ denotes a hydrogen atom or a methyl group, preferably a methyl group,
R'$_4$, R'$_5$ and R'$_6$, which may be identical or different, each denote a C$_1$ to C$_4$ alkyl group, preferably a methyl group,
A$_1$ denotes a linear or branched C$_1$ to C$_4$ alkylene group, preferably an ethylene group, and
X$_1^-$ denotes an anion, preferably a halide, particularly chloride.

In an embodiment, the at least one cationic thickening agent comprising at least one unit derived from acrylic or methacrylic acid is selected from homopolymers that come from monomers having structure (I), copolymers based on acrylamide and monomers having structure (I) and their mixtures.

In an embodiment, the at least one cationic thickening agent comprising at least one unit derived from acrylic or methacrylic acid is selected from homopolymers based on the polymerization of monomers having structure (I), copolymers based on copolymerization between at least one monomer having structure (I) and acrylamide, and their mixtures.

In an embodiment, the at least one cationic thickening agent comprising at least one unit derived from acrylic or methacrylic acid is selected from homopolymers based on polymerization of monomers having structure (I), methacryloyloxyethyl trimethyl ammonium chloride, copolymers based on copolymerization between monomers having structure (I) and acrylamide, methacryloyloxyethyl trimethyl ammonium chloride/acrylamide, and mixtures thereof.

In an embodiment, the at least one cationic thickening agent comprising at least one unit derived from acrylic or methacrylic acid that is the homopolymer resulting from polymerization of monomers having structure (I) is polyquaternium-37.

In an embodiment, the at least one cationic thickening agent comprising at least one unit derived from acrylic or methacrylic acid that is the copolymer resulting from the copolymerization between monomers having structure (I) and acrylamide is Polyquaternium-32.

In an embodiment, the at least one cationic thickening agent comprising at least one unit derived from acrylic or methacrylic acid is present in an amount of about greater than 1.5% to about 3 wt. %, preferably about 1.7 to about 2.7 wt. %, more preferably, about 2 to about 2.5 wt. %, based on the total weight of the hair cosmetic composition.

In an embodiment, the at least one cationic surfactant is selected from:
quaternary ammonium salts corresponding to the general formula below:

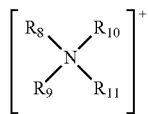

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms;
a quaternary ammonium salt of imidazoline;
a quaternary diammonium or triammonium salt, in particular of formula:

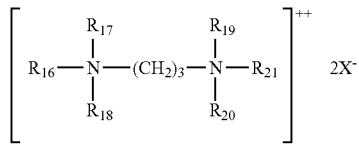

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18a})N-(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates; and
cationizable surfactants, including cationizable surfactants together with an acid neutralizer selected from compounds of the general structure $R_4$-A-$R_5$—B, wherein $R_4$ is a saturated or unsaturated, straight or branched alkyl chain with 8 to 24 C atoms, $R_5$ is a straight or branched alkyl chain with 1 to 4 C atoms, A is selected from:

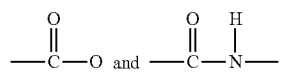

and B is selected from

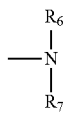

wherein $R_6$ and $R_7$ are the same or different is H or an alkyl chain with 1 to 4 C atoms, hydroxyl alkyl chain with 1 to 4 C atoms and di hydroxyl alkyl chain with 2 to 4 C atoms, and

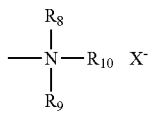

wherein $R_8$ and $R_9$ are the same or different, an alkyl chain with 1 to 4 C atoms, hydroxyl alkyl chain with 1 to 4 C atoms and di hydroxyl alkyl chain with 2 to 4 C atoms, $R_{10}$ is an alkyl chain with 1 to 4 C atoms, hydroxyl alkyl chain with 1 to 4 C atoms or di hydroxyl alkyl chain with 2 to 4 C atoms,
or mixtures thereof.

In an embodiment, the at least one cationic surfactant is selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyldiethylamine, arachidamidoethyldiethylamine, arachidamidoethyldimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

In an embodiment, the at least one cationic surfactant is present in an amount of about 0.2 to about 5 wt. %, preferably, about 0.5 to about 4 wt. %, more preferably, about 0.6 to about 3 wt. %, and even more preferably, about 0.6 to about 2 wt. %, such as from about 0.7 to about 1.5 wt. %, or such as about 0.7 to about 1 wt. %, based on the total weight of the hair cosmetic composition.

In an embodiment, the at least one fatty alcohol is selected from cetyl alcohol, stearyl alcohol, cetearyl alcohol (combination of cetyl alcohol and stearyl alcohol), behenyl alcohol, lauryl alcohol (1-dodecanol); myristic or myristyl alcohol (1-tetradecanol), arachidyl alcohol (1-eicosanol), lignoceryl alcohol (1-tetracosanol); ceryl alcohol (1-hexacosanol); montanyl alcohol (1-octacosanol); myricylic alcohol (1-triacontanol), decyl alcohol, undecyl alcohol, and a mixture thereof.

In an embodiment, the at least one fatty alcohol is present in an amount of about 0.5 to about 3 wt. %, or preferably, about 1 to about 2.7 wt. %, or more preferably, about 1.5 to about 2.5 wt. %, or even more preferably, about 1.7 to about 2.5 wt. %, such as from about 1.7 to about 2.3 wt. %, or such from about 2 to about 2.3 wt. %, based on the total weight of the hair cosmetic composition.

In an embodiment, the panthenol is present in an amount of about 0.1 to about 3 wt. %, or preferably, about 0.2 to about 2.7 wt. %, or more preferably, about 0.3 to about 2.5 wt. %, or even more preferably, about 0.4 to about 2 wt. %, based on the total weight of the hair cosmetic composition.

In an embodiment, the at least one amino functionalized silicone is selected from amodimethicone, bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof.

In an embodiment, the at least one amino functionalized silicone is present in an amount of about 0.1 to about 3 wt. %, or preferably about 0.3 to about 2.5 wt. %, or more preferably, about 0.5 to about 2 wt. %, based on the total weight of the hair cosmetic composition.

In an embodiment, the at least one plant or vegetable oil is selected from coconut oil, jojoba oil, argan oil, or mixtures thereof.

In an embodiment, the at least one plant or vegetable oil is coconut oil.

In an embodiment, the at least one plant or vegetable oil is present in an amount of about 0.1 to about 4.5 wt %, preferably, about 0.5 to about 4.5 wt. %, or more preferably, about 1 to about 4 wt. %, or even more preferably, about 2 to about 4 wt. %, based on the total weight of the hair cosmetic composition.

In an embodiment, the composition of the present invention further comprises at least one nonionic surfactant selected from alkoxylated fatty alcohols.

In an embodiment, the composition of the present invention further comprises at least one ester such as cetyl esters, isopropyl esters, glyceryl esters, and mixtures thereof.

In an embodiment, the hair cosmetic composition of the present invention typically includes:
  (a) at least one cationic vinylpyrrolidone copolymer selected from copolymers of vinylpyrrolidone and at least one monomer selected from the group consisting of (meth)acrylic acid; (meth)acrylates; unsaturated hydrocarbons; and vinyl monomers, preferably selected from VP/Dimethylaminoethylmethacrylate Copolymer and present in an amount of about 0.6 to about 1 wt. %, or about 0.6 to about 0.8 wt. %;
  (b) at least one cationic thickening agent comprising at least one unit derived from acrylic or methacrylic acid selected from homopolymers based on polymerization of monomers having structure (I), methacryloyloxyethyl trimethyl ammonium chloride, preferably selected from polyquaternium-37 and present in an amount of about 1.7 to about 2.7 wt. %, or about 2 to about 2.5 wt. %;
  (c) at least one cationic surfactant, including a cationizable surfactant and present in an amount of about 0.7 to about 1.5 wt. %, or about 0.7 to about 1 wt. %;
  (d) at least one fatty alcohol, present in an amount of about 0.5 to about 3 wt. %, or preferably, about 1 to about 2.7 wt. %, or more preferably, about 1.5 to about 2.5 wt. %, or even more preferably, about 1.7 to about 2.5 wt. %, such as from about 1.7 to about 2.3 wt. %, or such from about 2 to about 2.3 wt. %;
  (e) panthenol, present in an amount of about 0.1 to about 1 wt. %;
  (f) at least one amino functionalized silicone selected from selected from amodimethicone, bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof, preferably selected from amodimethicone;
  (g) at least one plant or vegetable oil, present in an amount of about 1 to about 4 wt. %, or about 2 to about 4 wt. %; and
  (h) water;
all weights being based on the total weight of the hair cosmetic composition.

In an embodiment, the present invention is further directed to a method of imparting to hair one or more of:
  night care benefits;
  hydration/moisturization;
  shaping or styling hold;
  frizz control;
  long-lasting frizz control;
  manageability;
  curl definition;
  curl retention;
  fast, easy styling/shaping benefits;
  long-lasting shape;
  humidity-resistant curl definition;
  volume control;
  smoothness;
  softness;
  natural feel;
  conditioning; or
  light-weight feel,
the method comprising applying onto hair, any one of the above-described hair cosmetic compositions of the present disclosure.

In an embodiment, the present invention is further directed to a method comprising applying a hair cosmetic composition comprising:
  (a) at least one cationic vinylpyrrolidone copolymer;
  (b) at least one cationic thickening agent comprising at least one unit derived from acrylic or methacrylic acid;
  (c) at least one cationic surfactant, including a cationizable surfactant;
  (d) at least one fatty alcohol, present in an amount of not more than about 3 wt. %;
  (e) panthenol, present in an amount of about 0.1 to about 1 wt. %;
  (f) at least one amino functionalized silicone;
  (g) at least one plant or vegetable oil, present in an amount of not more than about 4.5 wt. %; and
  (h) water;
all weights being based on the total weight of the hair cosmetic composition;
  wherein the weight ratio of the total amount of the at least one cationic vinylpyrrolidone copolymer and the at least one cationic thickening agent comprising at least one unit derived from acrylic or methacrylic acid to the total amount of the at least one amino functionalized silicone and to the at least one plant or vegetable oils is about 0.2 to about 0.8 or about 0.25 to about 0.6 or about 0.3 to about 0.5.

In an embodiment, the present invention is further directed to a method of preserving or maintaining the style or shape of hair that is exposed to prolonged external influences such as compression and/or humidity, the method comprising applying a hair cosmetic composition comprising:

(a) at least one cationic vinylpyrrolidone copolymer;
(b) the at least one cationic thickening agent comprising at least one unit derived from acrylic or methacrylic acid;
(c) at least one cationic surfactant, including a cationizable surfactant;
(d) at least one fatty alcohol, present in an amount of not more than about 3 wt. %;
(e) panthenol, present in an amount of about 0.1 to about 1 wt. %;
(f) at least one amino functionalized silicone;
(g) at least one plant or vegetable oil, present in an amount of not more than about 4.5 wt. %; and
(h) water;
all weights being based on the total weight of the hair cosmetic composition;
wherein the weight ratio of the total amount of the at least one cationic vinylpyrrolidone copolymer and the at least one cationic thickening agent comprising at least one unit derived from acrylic or methacrylic acid to the total amount of the at least one amino functionalized silicone and to the at least one plant or vegetable oils is about 0.2 to about 0.8 or about 0.25 to about 0.6 or about 0.3 to about 0.5.

The above compositions, which feature a unique combinations of ingredients, advantageously provide frizz control, volume control, curl definition, curl retention, curl pick-up, discipline, hold/control, styling/shaping, long lasting or humidity-resistant styling and curl care benefits together with natural feel, light-weight feel, non-oily or non-greasy feel, softness, and smoothness.

The hair cosmetic compositions described herein may be in any suitable physical form. Suitable forms include, but are not limited to low to moderate viscosity liquids, lotions, milks, gel creams, emulsion creams, pastes, clays, conditioners, masks, and the like.

The hair cosmetic compositions may be packaged in a variety of different containers, such as, for example, a ready-to-use container. Non-limiting examples of useful packaging include tubes, jars, caps, unit dose packages, and bottles, including squeezable tubes and bottles and spray bottles.

Cationic Vinylpyrrolidone Copolymer

The at least one cationic vinylpyrrolidone copolymer may be selected from copolymers of vinylpyrrolidone and at least one monomer selected from the group consisting of (meth) acrylic acid; (meth)acrylates; unsaturated hydrocarbons; and vinyl monomers.

In other words, the cationic vinylpyrrolidone copolymer may be obtained by co-polymerization of vinylpyrrolidone and at least one co-monomer selected from the group consisting of acrylic acid or methacrylic acid; acrylates or methacrylates; unsaturated hydrocarbons, preferably alkenes such as styrene, butadiene, hexadecene, eicosene, decene, and triacontene; and vinyl monomers.

As examples of the acrylates or methacrylates, mention may be made of methyl acrylate, ethyl acrylates, dimethylaminomethyl acrylate, dimethylaminoethyl acrylate, methyl methacrylate, ethyl methacrylates, dimethylaminomethyl methacrylate, dimethylaminoethyl methacrylate, quaternized dimethylaminomethyl methacrylate, quaternized dimethylaminoethyl methacrylate, and methacrylamidopropyltrimethylammonium.

As examples of the vinyl monomers, mention may be made of vinyl alcohol, vinyl acetate, vinyl propionate, vinyl neodecanoate, vinyl pivalate, vinyl benzoate, vinyl t-butyl benzoate, vinyl caprolactam and methylvinylimidazolium.

The cationic vinylpyrrolidone copolymer may be chosen from the group consisting of: vinylpyrrolidone copolymers comprising dimethylaminoethyl methacrylate units, vinylpyrrolidone copolymers comprising methacrylamidopropyltrimethylammonium units, and vinylpyrrolidone copolymers comprising methylvinylimidazolium units.

The cationic vinylpyrrolidone copolymers comprising dimethylaminoethyl methacrylate units may be chosen from:
vinylpyrrolidone/dimethylaminoethyl methacrylate copolymers; for example, vinylpyrrolidone/dimethylaminoethyl methacrylate copolymer (20/80 by weight) sold under the trade name Copolymer 845 by the company I.S.P.,
vinylpyrrolidone/dimethylaminoethyl methacrylate copolymers quaternized with diethyl sulphate; for example, vinylpyrrolidone/dimethylaminoethyl methacrylate copolymer quaternized with diethyl sulphate, sold under the trade names Gafquat 734, 755, 755S and 755L by the company I.S.P,
vinylpyrrolidone/dimethylaminoethyl methacrylate/hydrophilic polyurethane copolymers; for example, vinylpyrrolidone/dimethylaminoethyl methacrylate/hydrophilic polyurethane copolymer, sold under the trade name Pecogel GC-310 by the company U.C.I. B., or under the trade names Aquamere C 1031 and C 1511 by the company Blagden Chemicals,
vinylpyrrolidone/dimethylaminoethyl methacrylate/C8-C16 olefin copolymers, quaternized or non-quaternized; for example, vinylpyrrolidone/dimethylaminoethyl methacrylate/C8-C16 olefin copolymer sold under the trade names Ganex ACP1050 to 1057, 1062-1069 and 1079-1086 by the company I.S.P., and
vinylpyrrolidone/dimethylaminoethyl methacrylate/vinylcaprolactam copolymers; for example, vinylpyrrolidone/dimethylaminoethyl methacrylate/vinylcaprolactam copolymer sold under the trade name Gaffix VC713 by the company I.S.P.

The cationic vinylpyrrolidone copolymers comprising methacrylamidopropyltrimethylammonium (MAPTAC) units may be chosen from:
vinylpyiTolidone/methaciylamidopropyltrimethylammonium copolymers; for example, vinylpyrrolidone/MAPTAC copolymer sold under the trade names Gafquat ACP1011 and Gafquat HS100 by the company I.S.P.,
and
vinylpyrrolidone/methaciylamidopropyltrimethylammonium/vinylcaprolactam terpolymers; for example, vinylpyrrolidone/MAPTAC/vinylcaprolactam terpolymer sold under the trade names Polymer ACP 1059, 1060 and 1156 by the company I.S.P. The cationic vinylpyrrolidone copolymers comprising methylvinylimidazolium units may be chosen from vinylpyrrolidone/methylvinylimidazolium chloride copolymers; for example, vinylpyrrolidone/methylvinylimidazolium chloride copolymer sold under the trade names Luviquat FC370, FC550, FC905 and HM552 by the company BASF, vinylpyrrolidone/methylvinylimidazolium chloride/vinylimidazole copolymers; for example, vinylpyrrolidone/methylvinylimidazolium chloride/vinylimidazole copolymer sold under the trade name Luviquat 8155 by the company BASF, vinylpyrrolidone/vinyl caprolactam/vinylimidazolium copolymers; for example, vinylpyrrolidone/ vinylcaprolactam/vinylimidazolium methosulfate copolymer sold under the trade name Luviquat Hold by the company BASF, and vinylpyrrolidone/methylvinylimidazolium methosulphate copolymers; for example, vinylpyrrolidone/methylvinylimidazolium methosulphate copolymer sold under the trade name Luviquat MS370 by the company BASF.

It may be preferable that the cationic vinylpyrrolidone copolymer be chosen from vinylpyrrolidone polymers comprising dimethylaminoethyl methacrylate units, more preferably chosen from vinylpyrrolidone/dimethylaminoethyl methacrylate copolymers, for example those sold under the name COPOLYMER 845-0 by the company ISP ASHLAND.

It may be preferable that the cationic vinylpyrrolidone copolymer be chosen from vinylpyrrolidone polymers comprising methacrylamidopropyltrimethylammonium units, and more preferably Polyquaternium-28.

It may also be preferable that the cationic vinylpyrrolidone copolymer be chosen from vinylpyrrolidone polymers comprising methylvinylimidazolium units, more preferably chosen from vinylpyrrolidone/methylvinylimidazolium copolymers, and even more preferably Polyquaternium-16 for example those sold under the trade name LUVIQUAT FC 370 by the company AROMAT.

The total amount of the cationic vinylpyrrolidone copolymer in the composition, if present, may vary but is typically from greater than 0.4 to about 2 wt. %, based on the total weight of the composition. In some instances, the total amount of cationic vinylpyrrolidone copolymer is in an amount of about 0.45 to about 2 wt. %, preferably, about 0.6 to about 1.5 wt. %, more preferably, about 0.6 to about 1 wt. %, based on the total weight of the composition, including ranges and sub-ranges there between.

Thus, the cationic vinylpyrrolidone copolymer is present, by weight, based on the total weight of the composition, in an amount from about 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, to about 2 wt. %, including increments and ranges therein and there between.

Cationic Thickening Agent

The cationic thickening agent comprising at least one unit derived from acrylic or methacrylic acid of the compositions of the present invention is selected from the polymers resulting from polymerization of one or more monomers, including one or more monomers having structure (I):

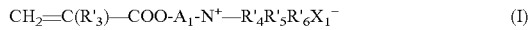

$$CH_2=C(R'_3)-COO-A_1-N^+-R'_4R'_5R'_6X_1^-  \quad (I)$$

in which:
- $R'_3$ denotes a hydrogen atom or a methyl group, preferably a methyl group,
- $R'_4$, $R'_5$ and $R'_6$, which may be identical or different, each denote a $C_1$ to $C_4$ alkyl group, preferably a methyl group,
- $A_1$ denotes a linear or branched $C_1$ to $C_4$ alkylene group, preferably an ethylene group, and
- $X_1^-$ denotes an anion, preferably a halide, particularly chloride.

The cationic thickening agent or agents according to the invention may be crosslinked or not.

Preferably, the cationic thickening agent or agents are chosen from homopolymers that come from monomers having structure (I), copolymers based on acrylamide and monomers having structure (I) and their mixtures.

In other words, the cationic thickening agent or agents are chosen from homopolymers based on the polymerization of monomers having structure (I), copolymers based on copolymerization between at least one monomer having structure (I) and acrylamide, and their mixtures.

Among homopolymers based on polymerization of monomers having structure (I), methacryloyloxyethyl trimethyl ammonium chloride, INCI name Polyquaternium-37 homopolymer is preferred.

Among copolymers based on copolymerization between monomers having structure (I) and acrylamide, methacryloyloxyethyl trimethyl ammonium chloride/acrylamide, INCI name Polyquaternium-32, is preferred.

Preferably, the cationic thickening agent is the homopolymer of methacryloyloxyethyl trimethyl ammonium chloride, INCI Polyquaternium-37, which is commercially available under the tradename SYNTHALEN CR form the company 3V or the tradename SALCARE SC 96 from the company BASF or the tradename SALCARE SC 95. SALCARE SC 96 is available as a blend of polyquaternium-37, propylene glycol and PPG-1 trideceth-6.

The total amount of the cationic thickening agent in the composition, if present, may vary but is typically greater than 1.5% to about 3 wt. %, based on the total weight of the composition. In some instances, the total amount of cationic thickening agent(s) is from about 1.6 to about 3 wt. %, preferably about 1.7 to about 2.7 wt. %, more preferably, about 2 to about 2.5 wt. %, based on the total weight of the composition, including ranges and sub-ranges there between.

Thus, the cationic thickening agent is present, by weight, based on the total weight of the composition, in an amount from about 1.6, 1.65, 1.7, 1.75, 1.8, 1.85, 1.9, 1.95, 2, 2.1, 2.2, 2.3, 2.4, 2.5, 2.6, to about 2.7 wt. %, including increments and ranges therein and there between.

Cationic Surfactants Including Cationizable Surfactants

In accordance with the disclosure, compositions hereof may include at least one cationic surfactant. The term "cationic surfactant" means a surfactant that may be positively charged when it is contained in the compositions according to the disclosure. This surfactant may bear one or more positive permanent charges or may contain one or more functional groups that are cationizable in the composition according to the disclosure. Non-limiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

In some embodiments, the cationic surfactant is selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof.

In some embodiments, the cationic surfactant comprises cetrimonium chloride, behentrimonium chloride, and mixtures thereof. Behentrimonium Chloride, also described by the technical names that include 1-Docosanaminium, N,N,N-Trimethyl-, Chloride, and N,N,N-Trimethyl-1-Docosanaminium Chloride, is the quaternary ammonium salt that conforms to the formula:

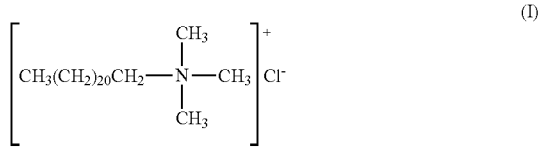

(I)

In accordance with some embodiments, the amount of each of the at least one cationic surfactant is from about 0.2 to about 5 wt. %, preferably, about 0.5 to about 4 wt. %, and more preferably, about 0.6 to about 3 wt. %, or any suitable combination, sub-combination, range, or sub-range thereof by weight, based on the weight of the composition. One of ordinary skill in the art, however, will appreciate that other ranges are within the scope of the invention. In some particular embodiments, the at least one cationic surfactant, including cationizable surfactants together with an acid neutralizer, is present from about 0.5 to about 5 wt. %, and in some particular embodiments is present from about 1 to about 3 wt. %, and when present, an acid neutralizer is present from about 0.1 to about 0.5 wt. %, based on the weight of the composition.

Thus, any one of the at least one cationic surfactant is present, by weight, based on the total weight of the composition, from about 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.4, 2.5, 2.6, 2.7, 2.8, 2.9, 3, 3.2, 3.4, 3.5, 3.6, 3.8, 4, 4.2, 4.4, 4.5, 4.6, 4.8, to about 5 wt. %, including increments and ranges therein and there between.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The cationic surfactant(s) may also be chosen from optionally polyoxyalkylenated, primary, secondary or tertiary fatty amines, or salts thereof, and quaternary ammonium salts, and mixtures thereof.

In some cases, it is useful to use salts such as chloride salts of the quaternary ammonium compounds.

The fatty amines generally comprise at least one $C_8$-$C_{30}$) hydrocarbon-based chain.

A. Examples of quaternary ammonium salts that may especially be mentioned include: those corresponding to the general formula below:

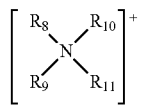

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and, in some embodiments, from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyal, $C_1$-$C_{30}$ alkoxy, polyoxy ($C_2$-$C_6$)alkylene, $C_1$-$C_{30}$ alkylamide, ($C_{12}$-$C_{22}$)alkylamido ($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (III), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

B. a quaternary ammonium salt of imidazoline, such as, for example, those of formula below:

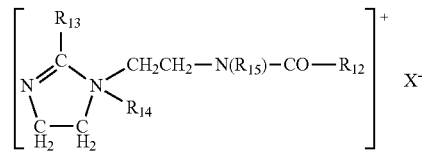

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylaryl-sulfonates in which the alkyl and aryl groups, in some embodiments, comprise, respectively, from 1 to 20 carbon atoms and from 6 to 30 carbon atoms. $R_{12}$ and $R_{13}$, in some embodiments, denote a mixture of alkenyl or alkyl groups containing from 12 to 21 carbon atoms, derived for example from tallow fatty acids, $R_{14}$, in some embodiments, denotes a methyl group, and $R_{15}$, in some embodiments, denotes a hydrogen atom. Such a product is sold, for example, under the name REWOQUAT W 75 by the company Rewo;

C. a quaternary diammonium or triammonium salt, in particular of formula:

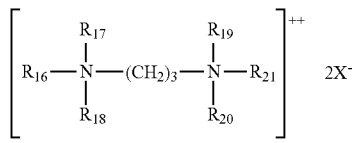

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18a})N$—$(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75), D. Cationic/cationizable surfactants, including cationizable surfactants together with an acid neutralizer, for example of the general structure R4-A-R5B wherein R4 is a saturated or unsaturated, straight or branched alkyl chain with 8 to 24 C atoms, R5 is a straight or branched alkyl chain with 1 to 4 C atoms, A is selected from:

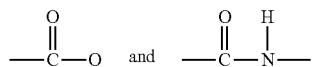

and B is selected from

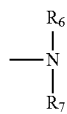

wherein $R_6$ and $R_7$ are the same or different is H or an alkyl chain with 1 to 4 C atoms, hydroxyl alkyl chain with 1 to 4 C atoms and di hydroxyl alkyl chain with 2 to 4 C atoms, and

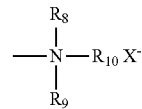

wherein $R_8$ and $R_9$ are the same or different, an alkyl chain with 1 to 4 C atoms, hydroxyl alkyl chain with 1 to 4 C atoms and di hydroxyl alkyl chain with 2 to 4 C atoms, R.sub.10 is an alkyl chain with 1 to 4 C atoms, hydroxyl alkyl chain with 1 to 4 C atoms or di hydroxyl alkyl chain with 2 to 4 C atoms.

In some instances, $R_4$ is saturated or unsaturated, straight or branched alkyl chain with 10 to 24C atoms, in some embodiments, 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidoprooyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, steara midopropyl diethylamine, stearamidopropylcibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, beherylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, beherylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulrate, and dicocoylethylhydroxyethylmonium methosulfate.

Cationizable surfactants or amphiphilic surfactants may be chosen from fatty alkylamines. in some embodiments, fatty dialkylamines. In some cases, the fatty dialkylamines may be fatty dimethylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures thereof are useful, especially in combination with fatty dimethylamines such as, for example, stearamidopropyl dimethylamine.

Fatty Alcohol

In accordance with the disclosure, compositions hereof include at least one fatty alcohol.

The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

The fatty alcohol(s) may be liquid or solid. In some instances, it is preferable that the hair cosmetic compositions include at least one solid fatty alcohol. The solid fatty alcohols that can be used include those that are solid at ambient temperature and at atmospheric pressure (25° C., 780 mmHg), and are insoluble in water, that is to say they have a water solubility of less than 1% by weight, preferably less than 0.5% by weight, at 25° C., 1 atm.

The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

In particular, it is possible to mention, alone or as a mixture: lauryl alcohol or lauryl alcohol (1-dodecanol); myristic or myristyl alcohol (1-tetradecanol); cetyl alcohol (1-hexadecanol); stearyl alcohol (1-octadecanol); arachidyl alcohol (1-eicosanol); behenyl alcohol (1-docosanol); lignoceryl alcohol (1-tetracosanol); ceryl alcohol (1-hexacosanol); montanyl alcohol (1-octacosanol); myricylic alcohol (1-triacontanol).

Preferably, the solid fatty alcohol is chosen from cetyl alcohol, stearyl alcohol, behenyl alcohol and mixtures thereof such as cetylstearyl or cetearyl alcohol.

The liquid fatty alcohols, in particular those containing C10-C34, preferably have branched carbon chains and/or have one or more, preferably 1 to 3 double bonds. They are preferably branched and/or unsaturated (C=C double bond), and contain from 12 to 40 carbon atoms.

The liquid fatty alcohols may be represented by: R—OH, wherein R denotes a C12-C24 branched alkyl group or an alkenyl group (comprising at least one C12-C24 double bond C=C), R being optionally substituted by one or more hydroxy groups. Preferably, the liquid fatty alcohol is a branched saturated alcohol. Preferably, R does not contain a hydroxyl group. These include oleic alcohol, linoleic alcohol, linolenic alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and mixtures thereof. Preferably, the liquid fatty alcohol is 2-octyl-1-dodecanol.

In some instances, the hair cosmetic compositions include one or more fatty alcohols selected from decyl alcohol, undecyl alcohol, dodecyl, myristyl, cetyl alcohol, stearyl alcohol, cetearyl alcohol, isostearyl alcohol, isocetyl alcohol, behenyl alcohol, linalool, oleyl alcohol, myricyl alcohol and a mixture thereof. In some instances, the hair cosmetic compositions preferably include cetearyl alcohol.

In accordance with the various embodiments, when present, the amount of each of the at least one fatty alcohol is from about 0.5 to about 3 wt. %, or preferably, about 1 to about 2.7 wt. %, or more preferably, about 1.5 to about 2.5 wt. %, or any suitable combination, sub-combination, range, or sub-range thereof by weight, based on the weight of the composition.

Thus, any one of the at least one fatty alcohol is present, by weight, based on the total weight of the composition, in an amount of from about 0.5, 0.6, 0.7, 0.8, 0.9, 1, 1.1, 1.2, 1.4, 1.5, 1.6, 1.7, 1.8, 1.9, 2, 2.1, 2.2, 2.3, 2.4, 2.5, 2.6, 2.7, 2.8, 2.9, to about 3 wt. %, including increments and ranges therein and there between.

Panthenol

In an embodiment, panthenol is present in an amount of about 0.1 to about 3 wt. %, or preferably, about 0.2 to about 2.7 wt. %, or more preferably, about 0.3 to about 2.5 wt. %, or even more preferably, about 0.4 to about 2 wt. %, based on the total weight of the hair cosmetic composition, including ranges and sub-ranges there between.

Thus, panthenol is present, by weight, based on the total weight of the composition, in an amount of from about 0.1, 0.15, 0.2, 0.25, 0.3, 0.35, 0.4, 0.45, 0.5, 0.55, 0.6, 0.65, 0.7, 0.75, 0.8, 0.9, 0.95, 1, 1.1, 1.2, 1.4, 1.5, 1.6, 1.7, 1.8, 1.9, 2, 2.1, 2.2, 2.3, 2.4, 2.5, 2.6, 2.7, 2.8, 2.9, to about 3 wt. %, including increments and ranges therein and there between.

Amino Functionalized Silicones

The silicones may be hydrophobic or, in some instances, be functionalized to be hydrophilic. Preferably, the silicones of the hair treatment compositions are amino functionalized silicone. The term "amino-functionalized silicone" means a silicone containing at least one primary amino, secondary amino, tertiary amino and/or quaternary ammonium group. The structure of the amino-functionalized silicone may be linear or branched, cyclic or non-cyclic. The amino functional group may be at any position in the silicone molecule, preferably at the end of the backbone (for example, in the case of amodimethicones) and/or in the side chain.

In some instances, the amino-functionalized silicones are selected from compounds of the following formula:

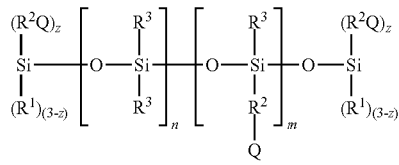

wherein each $R^1$ is independently selected from a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$ alkaryl group, a $C_{1-30}$ alkoxyaryl group, and a hydroxy group (preferably, each $R^1$ is independently selected from a $C_{1-30}$ alkyl group, a $C_{1-30}$ alkoxy group and a hydroxy group);

each $R^2$ is independently a divalent alkylene radical having one to ten carbon atoms (preferably, $R^2$ is a divalent alkylene radical having three to six carbon atoms);

each $R^3$ is independently selected from a $C_{1-30}$ alkyl group, a $C_{5-30}$ aryl group, a $C_{6-30}$ aralkyl group and a $C_{1-30}$ alkaryl group (preferably, each $R^3$ is independently selected from a $C_{1-30}$ alkyl group);

Q is a monovalent radical selected from $-NR^4{}_2$ and $-NR^4(CH_2)_xNR^4{}_2$;

each $R^4$ is independently selected from a hydrogen and a $C_{1-4}$ alkyl group;

x is 2 to 6;

z is 0 or 1;

n is 25 to 3,000 (preferably, 25 to 2,000; more preferably, 25 to 1,000; most preferably 25 to 500); and m is 0 to 3,000 (preferably, 0 to 2,000; more preferably, 0 to 1,000; most preferably, 0 to 100);

with the proviso that at least 50 mol % of the total number of $R^1$ and $R^3$ groups are methyl and with the proviso that when m is 0, z is 1.

Preferred $R^1$ groups include methyl, methoxy, ethyl, ethoxy, propyl, propoxy, isopropyl, isopropoxy, butyl, butoxy, isobutyl, isobutoxy, phenyl, xenyl, benzyl, phenylethyl, tolyl and hydoxy. Preferred $R^2$ divalent alkylene radicals include trimethylene, tetramethylene, pentamethylene, $-CH_2CH(CH_3)CH_2-$ and $-CH_2CH_2CH(CH_3)CH_2-$. Preferred $R^3$ groups include methyl, ethyl, propyl, isopropyl, butyl, isobutyl, phenyl, xenyl, benzyl, phenylethyl and tolyl. Preferred $R^4$ groups include methyl, ethyl, propyl, isopropyl, butyl and isobutyl. When z is 0, the amino-functionalized silicone has only pendant amine functional substituents in the polymer chain. When z is 1, the amino-functional silicone may have only terminal amine functional substituents (e.g., m=0) or may have both terminal and pendant amine functional substituents in the polymer chain (e.g., m>0). Preferably, n+m is 50 to 1,000. More preferably, n+m is 50 to 750. Still more preferably, n+m is 50 to 500. Most preferably, n+m is 50 to 250.

In some instances, the amino-functionalized silicones are alkoxylated and/or hydroxylated amino silicones. Suitable alkoxylated and/or hydroxylated amino silicones may be selected from compounds having a structure in accordance with the following formula:

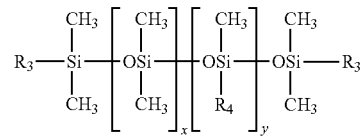

wherein $R_3$ is hydroxyl or $OR_5$, $R_5$ is a $C_1$ to $C_4$ alkyl group, $R_4$ is a group with a structure according to the following formula:

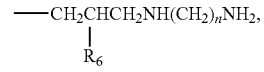

wherein $R_6$ is a $C_1$ to $C_4$ alkyl, n is a 1 to 4, x is the same as "n" described above, and y is the same as "m" described above.

Non-limiting examples of amino-functionalized silicones include bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof. In some instances, a particularly useful amino-functionalized silicone is bis-hydroxy/methoxy amodimethicone, wherein X is isobutyl and one of the R is OH and the other is $OCH_3$ in the above structure, also known as "Bis-Hydroxy/Methoxy Amodimethicone" and "3-[(2-aminoethyl)amino]-2-methylpropyl Me, di-Me, [(hydroxydimethylsilyl)oxy]- and [(methoxydimethylsilyl)oxy]-terminated." Bis-hydroxy/methoxy amodimethicone is commercially available under the tradename DOWSIL AP-8087 FLUID from The Dow Chemical Company.

The silicone of the hair treatment composition may, in some instances, include polydiorganosiloxanes, e.g., polydimethylsiloxanes having the CTFA designation dimethicone. Additional silicones that may be suitable for the hair treatment compositions include (particularly for shampoos and conditioners) polydimethyl siloxanes having hydroxyl end groups, which have the CTFA designation dimethiconol. Silicone gums may, in some instances, be included in the hair treatment compositions, such as those having a slight degree of cross-linking. Non-limiting examples of silicone gums that may, optionally, be included are described in WO 96/31188, which is incorporated herein by reference for all purposes.

The silicone(s) may have a viscosity of at least 10,000 cst, such as at least 50,000 cst, at least 100,000 cst, at least 200,000 cst, at least 400,000 cst, at least 800,000 cst, at least 1,000,000 cst, or at least 2,000,000 cst. Preferably the viscosity does not exceed $10^9$ cst for ease of formulation.

The hair treatment composition may include pre-formed emulsions of silicones, such as emulsions DC2-1766, DC2-1784, and microemulsions DC2-1865 and DC2-1870 from Dow Corning, or cross-linked silicone gums, such as DC X2-1787 or DC X2-1391 from Dow Corning.

In accordance with the various embodiments, when present, the amount of the at least one amino functionalized silicone is from about 0.1 to about 3 wt. %, or preferably about 0.3 to about 2.5 wt. %, or more preferably, about 0.5 to about 2 wt. %, or any suitable combination, sub-combination, range, or sub-range thereof by weight, based on the weight of the composition. One of ordinary skill in the art, however, will appreciate that other ranges are within the scope of the invention. In some particular embodiments, at least one amino functionalized silicone is present from about 0.5 wt. % to about 15%, and in some particular embodiments present from about 1% to about 5 wt. %.

Thus, any one of the at least one amino functionalized silicone is present, by weight, based on the total weight of the composition, in an amount of from about 0.1, 0.2, 0.3, 0.4, 0.5, 0.6, 0.7, 0.8, 0.9, 1, 1.1, 1.2, 1.4, 1.5, 1.6, 1.8, 2, 2.1, 2.2, 2.3, 2.4, 2.5, 2.6, 2.7, 2.8, 2.9, to about 3 wt. %, including increments and ranges therein and there between.

Plant or Vegetable Oils

The plant or vegetable oils of the compositions of the present invention include coconut oil, jojoba oil, argan oil, or mixtures thereof.

The total amount of the plant- or vegetable-based fatty component in the composition, if present, may vary but is typically from of about 0.1 to about 4.5 wt %, or about 0.5 to about 4.5 wt. %, or about 1 to about 4 wt. %, or about 1.5 to about 4 wt. %, or about 1.8 to about 4 wt. %, or about 2 to about 4 wt. %, based on the total weight of the composition, including ranges and sub-ranges there between.

Thus, the plant- or vegetable-based fatty component is present, by weight, based on the total weight of the composition, in an amount from about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4 to about 4.5 wt. %, including increments and ranges therein and there between.

Oils Other than Coconut Oil, Jojoba Oil, or Argan Oil

Other plant- or vegetable-based oils may be included in the fatty component of the compositions of the present invention, as long as they do not result in a composition that is greasy or oily or heavy on the hair.

Additional Ingredients

The compositions of the present invention may further comprise additional/optional ingredients such as nonionic surfactants, esters, and mixtures thereof.

The nonionic surfactants may be selected from alkoxylated fatty alcohols such as oleth-3, oleth-10, oleth-20, trideceth-5, trideceth-6, trideceth-10, PPG-1 trideceth-6, laureth-12, steareth-20, and combinations thereof, The esters may be selected from fatty esters, isopropyl esters, glyceryl (glycerol) esters, cetyl esters, caprlyic/capric triglycerides, and mixtures thereof.

The total amount of the optional additional ingredients in the composition, if present, may vary but is typically from about 0.01 to about 5 wt %, such as about 0.05 to about 4.5 wt. %, or such as about 1 to about 4 wt. %, based on the total weight of the composition, including ranges and sub-ranges there between.

Water

The amount of water in the hair cosmetic compositions may be at least 50 wt. %, or from about 50 to about 95 wt. %, about 50 to about 90 wt. %, about 60 to about 88 wt. %, about 70 to about 85 wt. %, based on the weight of the composition, including ranges and sub-ranges there between.

Organic Solvents

The hair-treatment compositions may optionally include at least one organic solvent (non-silicone solvents).

Non-limiting examples of organic solvents include, for example, alcohols (for example, $C_{1-15}$, $C_{1-10}$, or $C_{1-6}$ alcohols), organic solvents, polyols (polyhydric alcohols and glycols (e.g., glycerin, butylene glycol, caprylyl glycol, etc.), and a mixture thereof.

Non-limiting examples of organic solvents include monoalcohols and polyols such as ethyl alcohol, isopropyl alcohol, propyl alcohol, benzyl alcohol, and phenylethyl alcohol, or glycerin or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of organic solvents include alkanediols such as 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The total amount organic solvent(s) in the hair cosmetic composition, if present, can vary but is typically about 0.01 to about 10 wt. %, based on the total weight of the hair cosmetic composition. In some cases, the total amount of water-soluble solvent(s) is about 0.05 to about 8 wt. %, about 0.1 to about 6 wt. %, about 0.1 to about 0.5 to about 10 wt. %, about 0.5 to about 8 wt. %, about 0.5 to about 6 wt. %, about 0.5 to about 5 wt. %, about 1 wt. %, about 2 wt. %, about 3 wt. %, or about 4 wt. %, including all ranges and subranges there between.

Other Components

In one or more embodiments, the hair cosmetic compositions described herein may contain one or more additional ingredients (additives and miscellaneous ingredients). Examples include, but are not limited to surfactants, emulsifiers, thickeners (such as polysaccharide-based thickeners), film formers, other polymers, proteins, hydrolyzed proteins, amino acids, fragrance, pH adjusters, and preservatives. Additional details regarding such additional ingredients follows below.

In an embodiment, the compositions of the present disclosure are in the form of a leave-on cream product such as a styling/shaping product, leave-on product for curly hair (such as combing creams), anti-frizz hair product, or rinse-off or leave-on mask product.

In an embodiment, the compositions of the present disclosure are in the form of a rinse-off cream product such as a mask product.

In an embodiment, the compositions of the present disclosure are in the form of a leave-on cream product such as a styling/shaping product.

In an embodiment, the compositions of the present disclosure are in the form of a leave-on cream product such as a styling/shaping and conditioning product.

In an embodiment, the compositions of the present disclosure are in the form of a leave-on or a rinse-off styling conditioner.

In an embodiment, the compositions of the present disclosure are in the form of an emulsion such as an oil-in-water emulsion or a water-in-oil emulsion. In an embodiment, the emulsion is in the form of a cream.

In an embodiment, the compositions of the present disclosure are in the form of a gel cream.

Methods

Another aspect of the invention pertains to methods of using the hair cosmetic compositions described herein. The methods generally comprise applying any of the hair cosmetic compositions described to hair. The hair cosmetic compositions may be useful in a variety of settings, and either for chemically treated or untreated hair. Use on treated hair can include chemically relaxed/straightened hair or chemically dyed or bleached or lightened/highlighted hair. Use on hair may include as part of a shampoo, part of a conditioner or as a conditioner, as a pre-treatment, or after cleansing or conditioning or washing the hair as a leave-on treatment for styling/shaping the hair or caring for curly hair or as a leave-on or rinse-off mask treatment.

Methods of treating hair according to the disclosure may include applying a hair cosmetic composition of the instant disclosure to the hair (wet, damp, or dry hair), allowing the hair treatment to remain on the hair for a sufficient amount of time, and rinsing the hair cosmetic composition from the hair or allowing the hair treatment to be left on the hair as a leave-on product. The hair cosmetic composition may be applied to the hair before, during, or after other hair cosmetic compositions (e.g., a shampoo, a conditioner, a mask, a cream, a lotion, a gel, etc.).

Other methods of treating hair according to the disclosure involve a wash and go/braiding technique. Typically, the hair type on which this method is used is curly hair.

Other methods of treating hair according to the disclosure involve a twist out technique. Typically, the hair type on which this method is used is curly hair.

The hair cosmetic composition may be allowed to remain on the hair for a period of time, for example from about a few seconds (1, 3, 5, or 10 seconds) to about 10, 20, or 30 minutes, or longer such as up to about one hour or up to about two hours or up to about three hours or up to about four hours or up to about five hours or up to about six hours or up to about seven hours or up to about eight hours or up to about 12 hours.

The hair cosmetic compositions may be useful for treating chemically treated hair.

Described above is the individual application of a hair cosmetic composition or the combined or layered application of a hair cosmetic composition with another composition. In some cases, a hair cosmetic composition is individually applied to the hair and also combined or layered with another composition that is also applied to the hair.

Kits

The hair cosmetic compositions of the instant disclosure may be incorporated into a kit. For example, the kits may include at least one hair cosmetic composition according to the instant disclosure. The kits may also include one or more hair cosmetic compositions (according the instant disclosure), a shampoo and/or a conditioner and/or a mask.

Implementation of the present disclosure is provided by way of the following examples. The examples serve to illustrate the technology without being limiting in nature.

EXAMPLES

The following Examples are intended to be non-restrictive and explanatory only. The ingredient amounts in the compositions/formulas described below are expressed in % by weight, based on the total weight of the composition.

Several formulas were produced having the ingredients as listed in the tables below. The balance of all formulas was water.

Example I: Compositions

TABLE 1

Formulation Examples

| | | FORMULAS A (INVENTION) AND B TO G (COMPARATIVE) | | | | | | |
|---|---|---|---|---|---|---|---|---|
| INGREDIENT TYPE | INGREDIENT INCI NAME | A invention | B | C | D | E | F | G |
| FIRST CATIONIC POLYMER | VP/DIMETHYLAMINOETHYLMETHACRYLATE COPOLYMER | 0.6-1 | — | — | 0.2-0.4 | 0.2-0.4 | 0.2-0.4 | 0.2-0.4 |
| SECOND CATIONIC POLYMER | POLYQUATERNIUM-37 | 2 | 2 | — | 0.3 | 0.3 | 0.5 | 0.5 |
| CATIONIC SURFACTANT | BEHENTRIMONIUM CHLORIDE AND/OR CETRIMONIUM CHLORIDE | 0.7-1 | — | 0.7-1 | 0.7-1 | 0.7-1 | 0.7-1 | 0.7-1 |
| | BEHENTRIMONIUM METHOSULFATE AND/OR HYDROXYETHYL OLEYL DIMONIUM CHLORIDE AND/OR BRASSICAMIDOPROPYL DIMETHYLAMINE | — | 1.5 | — | — | — | — | — |
| FATTY ALCOHOL | CETEARYL ALCOHOL | 1.7-2.3 | 1.7-2.3 | 5 | 6 | 6 | 6 | 6 |
| | STEARYL ALCOHOL | — | — | 1 | — | — | — | — |
| | PANTHENOL | 0.5 | — | — | — | — | — | — |
| AMINOSILICONE | AMODIMETHICONE | 0.1-3 | 0.1-3 | 0.1-3 | 0.1-3 | 0.1-3 | 0.1-3 | 0.1-3 |
| PLANT OR VEGETABLE OILS | COCOS NUCIFERA (COCONUT) OIL AND/OR OLEA EUROPAEA (OLIVE) FRUIT OIL AND/OR BUTYROSPERMUM PARKII (SHEA) BUTTER AND/OR SIMMONDSIA CHINENSIS (JOJOBA) SEED OIL AND/OR ARGANIA SPINOSA KERNEL OIL AND/OR MACADAMIA TERNIFOLIA SEED OIL AND/OR PRUNUS AMYGDALUS DULCIS (SWEET ALMOND) OIL | 4 | 6.1 | 0.03 | 3.5 | 3.5 | 3.5 | 3.5 |
| OTHER OILS | MINERAL OIL | — | 1.4 | 1.5 | — | — | — | — |
| ESTERS | CETYL ESTERS and/or ISOPROPYL MYRISTATE and/or SORBITAN OLEATE | 0.08 | −0.08 | — | 5.3 | 5.3 | 5.3 | 5.3 |
| | PROPYLENE GLYCOL DICAPRYLATE/DICAPRATE AND/OR HYDROGENATED STARCH HYDROLYSATE | 2.8 | 1.4 | — | 0.21 | 0.21 | 0.35 | 0.35 |
| OTHER POLYMERS, SILICONES | ACRYLATES COPOLYMER AND/OR DIMETHICONE | — | 0.12 | — | — | — | 0.5 | 0.5 |
| NONIONIC SURFACTANTS | TRIDECETH-10 AND/OR TRIDECETH-6 AND/OR TRIDECETH-5 AND/OR OLETH-20 AND/OR PPG-1 TRIDECETH-6 | 2.2 | 6.2 | 0.03 | 0.5 | 0.5 | 0.5 | 0.5 |
| ADDITIVES OR MISCELLANEOUS INGREDIENTS | ONE OR MORE OF PRESERVATIVES, PH ADJUSTERS, CHELANTS, COLORANTS, XYLOSE, SALT, FRAGRANCE, VITAMINS PLANT EXTRACTS/ PROTEINS/AMINO ACIDS/PROTEIN HYDROLYSATES | <5.0 | <5.0 | <5.0 | <5.0 | <5.0 | <5.0 | <5.0 |

TABLE 1-continued

Formulation Examples

| | | FORMULAS A (INVENTION) AND B TO G (COMPARATIVE) | | | | | | |
|---|---|---|---|---|---|---|---|---|
| INGREDIENT TYPE | INGREDIENT INCI NAME | A invention | B | C | D | E | F | G |
| ORGANIC SOLVENTS | DIPROPYLENE GLYCOL AND/OR CAPRYLYL GLYCOL AND/OR ISOPROPYL ALCOHOL AND/OR GLYCERIN | <10 | <0 | <10 | <10 | <10 | <10 | <10 |
| SOLVENT | WATER | QS 100 | QS 100 | QS 100 | QS 100 | QS 100 | QS 100 | QS 100 |

TABLE 2

Formula Texture and Observations the Next Day After Overnight Test

| Formulas from TABLE 1 | Texture | Cosmetic performance or effect on hair |
|---|---|---|
| A | Bouncy, creamy texture and emollient feel | Provided increased shaping/styling hold, more curl definition, and soft feel. Also had conditioning, anti-frizz, volume control, and anti-static properties |
| B | Not bouncy, emollient feel | Compared to Formula A, this formula was heavy, greasy feel on hair; did not give enough shaping/styling hold |
| C | Not bouncy, slight emollient feel | Compared to Formula A, also provided soft touch but significantly less better frizz control and volume control, curl definition, and curl retention |
| D | Not bouncy, slight emollient feel | Not tested overnight |
| E | Not bouncy, slight emollient feel | Not tested overnight |
| F | Not bouncy, slight emollient feel | Not tested overnight |
| G | Not bouncy, slight emollient feel | Not tested overnight |

Process of Making the Invention Composition

The invention formula A was prepared according to the following process:

Overnight Test Protocols

A. Swatch Testing

Test hair swatches were first treated with a rinse-out shampoo followed by a rinse-out conditioner. The hair swatches were towel-dried and then treated with the inventive composition or a comparative composition. To mimic overnight use (tossing and turning when asleep), the swatches were turned and rubbed against each other and a towel for ten times. The swatches were then left in a humidity chamber for 12 hours at 25° C. and 80% humidity.

B. Consumer Testing

Human female volunteers were instructed to follow their regular hair routine at night and then apply the invention/test formula to their hair. The women volunteers who were selected typically wash their hair at night, air dry or diffuse, and use leave-in styling products to achieve a curl end look at least 3× a week. Additional criteria of test subjects were of similar hair length, hair texture of normal to coarse, curl type of slightly curly to curly. They used the products at a minimum of 4-5 uses per product.

After their regular hair routine at night, the volunteers dispensed the desired amount of the invention/test formula (starting with a dime size and applying more as needed) in their hands, rubbed their hands together, and evenly applied the formula to damp or dry hair. They then styled their hair as they normally would before going to sleep.

Example II Testing the Invention Against Comparative Formula C

Tests on hair swatches were conducted according to Protocol A above. The test swatches were first treated with a shampoo, followed by a conditioner. Three of the swatches were treated with Formula A and another three of the swatches were treated with Formula C. The test formulas were tested as leave-in products (no immediate rinsing). FIG. 1 shows the performance of the test formulas on hair after overnight testing.

When comparing to invention to Formula C which also provides soft curls (soft to the touch), the inventors have observed that the invention formula provided significantly better frizz and volume control, as well as significantly better curl definition and curl retention.

Example III Consumer Testing

The invention formula was tested on the hair of women volunteers according to Protocol B above. The volunteers provided feedback on their perception of how the test formula performed on their hair.

TABLE 3

Results of the consumer test

| Consumer End Benefit | CONSUMER PERCEPTION | Formula A |
|---|---|---|
| Drying/Styling | Fast, easy styling in the morning | + |
| | Fast/similar dry time | + |
| | Able to achieve desired look | + |
| Hair Appearance | Curls are defined/uniform | + |
| | Frizz was controlled/tamed | + |
| | Hair doesn't fall flat overnight | − |
| | Conditioned, healthy appearance | + |
| | Natural, soft look, not stiff | + |
| Hair Feel | Smooth, soft | + |
| | Moisturized/not dry | + |
| | Clean, non-greasy | + |
| | Easy to detangle at night (after applying) | + |
| | Detangled during application (next morning after rewetting) | + |
| | No build up or residue | + |
| Lastingness | Lasting frizz control | + |
| | Lasting curl definition | +/− |
| | Stays clean, does not become greasy | + |
| | Consistent style from day to day | + |
| Application/Usage Experience | Easy to apply/distribute | + |
| | No transfer onto pillow/no wet pillow | + |
| | Appropriate amount of product required (more than dime size) | + |
| Product Aspects | Visually appealing | + |
| | Pleasant texture, met expectations | + |
| | Just right consistency | + |

The results in Table 3 above show that the inventors surprisingly discovered a combination of ingredients that resulted in compositions provided good styling and shaping hold, including curl definition, good frizz and volume control, and other cosmetic attributes to hair even when the hair was treated the night before with the invention formula and it was slept on overnight. For the attribute, "hair doesn't fall flat overnight", the rating was negative. However, while the product did not deliver volume during night, it still enabled consumers to fix their hair quickly in the morning because the volunteers did not have "big frizzy" hair in the morning, i.e., the product delivered volume control and lasting frizz control to hair overnight which was a main objective of the study. For the attribute "lasting curl definition", the rating of +/− shows that some volunteers may not necessarily be defining this attribute in the same way (either lasting through the night and through the next day or lasting only through the night).

Overall, the consumer perception was that upon getting up in the morning, the invention formula provided to the hair that was slept on the desired cosmetic benefits such as fast, easy styling in the morning, curl definition, lasting frizz control, conditioned, healthy appearance, natural and soft look, feelings of softness, smoothness, no product build-up, detangling, being moisturized, and being clean, consistent style, visually appealing appearance, and pleasant texture.

In summary, the examples above show that the inventors surprisingly discovered a combination of ingredients that resulted in compositions that when applied to hair provided good styling and shaping hold, including curl definition, good frizz and volume control, and other cosmetic attributes to hair even when the hair was slept on for several hours (whether at night or during the day).

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

The term "lasting" or "long lasting" or "durable" as used herein means that the cosmetic attribute or effect was observed up to about 30 minutes or up to about one hour or up to about two hours, or up to about three hours or up to about four hours or up to about five hours or up to about six hours or up to about seven hours or up to about eight hours or up to about 12 hours or after an overnight period from the time the composition of the present disclosure was applied to hair on the head of a person and the hair was subjected to changes in the hair shape or style or configuration, and/or to disturbance of the hair fibers and/or to movement of the hair fibers as a result of sleeping or lying down and resting the head on a bed or other surface or the back part of a seat and/or as a result of wearing a head cap or cover for at least 30 minutes up to several hours or overnight.

Some of the various categories of components identified for the hair-treatment compositions may overlap. In such cases where overlap may exist and the composition/product includes two overlapping components (or more than two overlapping components), an overlapping component does not represent more than one component. For example, a fatty acid may be defined as both a "fatty compound" and a "surfactant/emulsifier." If a particular composition/product includes both a fatty compound component and an emulsifier component, a single fatty acid can serve as only a fatty compound or a surfactant/emulsifier (a single fatty acid does not serve as both the fatty compound and the surfactant/emulsifier).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically points 1, 2, 3, 4 and 5, as well as sub-ranges such as 2-5, 3-5, 2-3, 2-4, 1-4, etc.; and points of 1, 2, 3, 4, and 5 includes ranges and sub-ranges of 1-5, 2-5, 3-5, 2-3, 2-4, 1-4, etc.

Other than in the operating examples, or where otherwise indicated, all numbers expressing quantities of ingredients and/or reaction conditions are understood to be modified by "about," whether or not expressly stated. Additionally, all numbers are intended to represent exact FIGURES as additional embodiments, whether or not modified by "about." For example, "an amount of about 1%" includes an amount of exactly 1%. As a further example, "an amount of 1%" includes an amount of about 1%. The term "about" is generally understood to encompass a range of +/−10% from the stated number, and is intended to cover amounts of +/−1%, 2%, 3%, 4%, 5%, 6%, 7%, 8%, 9%, and 10%.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

The term "substantially free" or "essentially free" as used herein means the specific material may be present in small amounts that do not materially affect the basic and novel characteristics of the claimed invention. For instance, there may be less than 2% by weight of a specific material added to a composition, based on the total weight of the compositions (provided that an amount of less than 2% by weight does not materially affect the basic and novel characteristics of the claimed invention. Similarly, the compositions may include less than 2 wt %, less than 1.5 wt %, less than 1 wt %, less than 0.5 wt %, less than 0.1 wt %, less than 0.05 wt %, or less than 0.01 wt %, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure.

The term "substantially free" or "essentially free" as used herein may also mean that the specific material is not added to the composition but may still be present in a raw material that is included in the composition.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair cosmetic composition comprising:
   (a) about 0.6 to about 1.5 wt. % of VP/dimethylaminoethylmethacrylate copolymer;
   (b) about 1.7 to about 2.7 wt. % of polyquaternium-37;
   (c) about 0.5 to about 4 wt. % of at least one cationic or cationizable surfactant surfactant;
   (d) about 0.5 to about 3 wt. % of at least one fatty alcohol;
   (e) about 0.1 to about 1 wt. % of panthenol;
   (f) about 0.5 to about 2 wt. % of amodimethicone;
   (g) from 1 to about 4 wt. % of at least one plant or vegetable oil;
   (h) about 1 to about 4 wt. % at least one nonionic surfactant, at least one fatty ester, or mixtures thereof;
   (i) about 0.01 to about 10 wt. % of at least one organic solvent; and
   (j) about 70 to about 90 wt. % of water;
      provided that (a) and (b) are in a weight ratio with (f) and (g) of about 0.3 to about 0.5;
      wherein the hair cosmetic composition is free of colorants and does not alter color of hair when applied to the hair, and all percentages by weight are based on a total weight of the hair cosmetic composition.

2. The hair cosmetic composition of claim 1, wherein the at least one cationic surfactant is selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, or mixtures thereof.

3. The hair cosmetic composition of claim 1, wherein the at least one fatty alcohol is selected from cetyl alcohol, stearyl alcohol, cetearyl alcohol, behenyl alcohol, lauryl alcohol, myristyl alcohol, arachidyl alcohol, lignoceryl alcohol, ceryl alcohol, montanyl alcohol, myricylic alcohol, decyl alcohol, undecyl alcohol, or mixtures thereof.

4. The hair cosmetic composition of claim 1, wherein the at least one plant or vegetable oil is in an amount of 2.5 to less than 4.0 wt. %.

5. The hair cosmetic composition of claim 1, wherein the at least one plant or vegetable oil is selected from coconut oil, jojoba oil, argan oil, or mixtures thereof.

6. The hair cosmetic composition of claim 1, wherein the at least one plant or vegetable oil includes coconut oil.

7. The hair cosmetic composition of claim 1, wherein the hair cosmetic composition is an oil-in-water emulsion.

8. The hair cosmetic composition of claim 1, wherein the at least one organic solvent is selected from glycerin, monoalcohols, polyhydric alcohols, glycols, or mixtures thereof.

9. The hair cosmetic composition of claim 1 comprising the at least one nonionic surfactant and the at least one nonionic surfactant is selected from alkoxylated fatty alcohols.

10. The hair cosmetic composition of claim 1 comprising at least one nonionic surfactant and at least one fatty ester.

11. The hair cosmetic composition of claim 1, further comprising:
    less than 5 wt. % of one or more preservatives, pH adjusters, chelants, xylose, salts, fragrances, vitamins, proteins, protein hydrolysates, amino acids, or a combination thereof.

12. A method for treating hair comprising applying the hair cosmetic composition of claim 1 to the hair.

13. A hair cosmetic composition consisting of:
    (a) VP/dimethylaminoethylmethacrylate copolymer;
    (b) polyquaternium-37;
    (c) at least one cationic or cationizable surfactant surfactant;
    (d) at least one fatty alcohol in an amount not more than 3 wt. %;
    (e) panthenol;
    (f) amodimethicone;
    (g) at least one plant or vegetable oil in an amount not more than 4.5 wt. %;
    (h) at least one nonionic surfactant, at least one fatty ester, or mixtures thereof;
    (i) at least one organic solvent;
    (j) water; and
    (k) less than 5 wt. % of one or more preservatives, pH adjusters, chelants, xylose, salts, fragrances, vitamins, proteins, protein hydrolysates, amino acids, or a combination thereof;
    wherein (a) and (b) are in a weight ratio with (f) and (g) of about 0.3 to about 0.8 and all percentages by weight are based on a total weight of the hair cosmetic composition.

14. The hair cosmetic composition of claim 13, wherein the at least one plant or vegetable oil is selected from coconut oil, jojoba oil, argan oil, or mixtures thereof.

15. The hair cosmetic composition of claim 13, wherein the at least one plant or vegetable oil includes coconut oil.

16. The hair cosmetic composition of claim 13, wherein the at least one nonionic surfactant is present.

17. The hair cosmetic composition of claim 16, wherein the at least one nonionic surfactant is selected from alkoxylated fatty alcohols.

18. The hair cosmetic composition of claim 13, wherein the hair cosmetic composition is an oil-in-water emulsion.

19. A method for treating hair comprising applying the hair cosmetic composition of claim 13 to the hair.

\* \* \* \* \*